United States Patent
Wang et al.

(10) Patent No.: US 8,461,402 B2
(45) Date of Patent: Jun. 11, 2013

(54) ISOMERIZATION OF 1,1,3,3-TETRAFLUOROPROPENE

(75) Inventors: Haiyou Wang, Amherst, NY (US); Konstantin A. Pokrovski, Orchard Park, NY (US); Hsueh Sung Tung, Getzville, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/587,182

(22) Filed: Aug. 16, 2012

(65) Prior Publication Data

US 2012/0310019 A1 Dec. 6, 2012

Related U.S. Application Data

(62) Division of application No. 12/686,857, filed on Jan. 13, 2010, now Pat. No. 8,288,598.

(60) Provisional application No. 61/145,333, filed on Jan. 16, 2009.

(51) Int. Cl.
*C07C 17/00* (2006.01)
(52) U.S. Cl.
USPC .......................................................... 570/236

(58) Field of Classification Search
None
See application file for complete search history.

(56) References Cited

U.S. PATENT DOCUMENTS

| | | | |
|---|---|---|---|
| 5,710,352 A | 1/1998 | Tung | |
| 5,811,603 A * | 9/1998 | Elsheikh | 570/166 |
| 5,895,825 A | 4/1999 | Elsheikh et al. | |
| 6,124,510 A | 9/2000 | Elsheikh et al. | |
| 6,472,573 B1 | 10/2002 | Yamamoto et al. | |
| 7,420,094 B2 * | 9/2008 | Petrov et al. | 570/151 |
| 7,485,760 B2 | 2/2009 | Wang et al. | |
| 7,563,936 B2 | 7/2009 | Wang et al. | |
| 7,728,183 B2 * | 6/2010 | Nappa et al. | 570/177 |
| 2008/0051610 A1 * | 2/2008 | Wang et al. | 570/156 |
| 2008/0051611 A1 | 2/2008 | Wang et al. | |
| 2008/0058562 A1 | 3/2008 | Petrov et al. | |
| 2008/0103342 A1 * | 5/2008 | Wang et al. | 570/256 |
| 2010/0022809 A1 * | 1/2010 | Cottrell et al. | 570/163 |
| 2010/0185027 A1 * | 7/2010 | Wang et al. | 570/151 |

* cited by examiner

*Primary Examiner* — Sudhakar Katakam
(74) *Attorney, Agent, or Firm* — Bruce O. Bradford

(57) ABSTRACT

The present invention involves methods for isomerization of 1234zc. Also provided are methods for managing 1,1,3,3-tetrafluoropropene produced as a byproduct in a process for synthesizing trans-1,3,3,3-tetrafluoropropene from 245fa, wherein 1234zc is converted into trans/cis-1234ze with the help of a catalyst in the absence of HF and in an isomerization reactor, or is converted into 1234zc and/or 245fa with the help of a catalyst in the presence of HF in a separate reactor or preferably in the same reactor of 245fa dehydrofluorination.

17 Claims, 3 Drawing Sheets

ISOMERIZATION OF 1,1,3,3-TETRAFLUOROPROPENE

CROSS-REFERENCE TO RELATED APPLICATIONS

This application is a Divisional of U.S. application Ser. No. 12/686,857, filed on Jan. 13, 2010 (now U.S. Pat. No. 8,288, 598), which claims priority benefit of U.S. Provisional Application No. 61/145,333, filed on Jan. 16, 2009, each of which is incorporated herein by reference.

BACKGROUND

1. Field of Invention

This invention relates to methods for producing hydrofluorocarbon compounds. More specifically, this invention relates to isomerization of hydrofluoroalkenes.

2. Description of Prior Art

Currently, there is a worldwide effort to develop hydrofluorocarbons (HFCs), or compounds containing only carbon, hydrogen and fluorine, for applications as refrigerants, blowing agents, solvents and diluents for gaseous sterilization. Unlike chlorofluorocarbons (CFCs) and hydrochlorofluorocarbons (HCFCs), both of which potentially damage the Earth's ozone layer, HFCs contain no chlorines and thus pose no threat to the ozone layer. In this regard, trans-1,3,3,3-tetrafluoropropene (trans-1234ze) is a compound that has the potential to be used as a zero Ozone Depletion Potential (ODP) and a low Global Warming Potential (GWP) refrigerant, blowing agent, aerosol propellant, solvent, etc., and also as a fluorinated monomer.

Methods for producing HFO-1234ze are known. For example, U.S. Pat. No. 5,710,352 teaches the fluorination of 1,1,1,3,3-pentachloropropane (HCC-240fa) to form HCFO-1233zd and a small amount of HFO-1234ze. U.S. Pat. No. 5,895,825 teaches the fluorination of HCFO-1233zd to form HFO-1234ze. U.S. Pat. No. 6,472,573 also teaches the fluorination of HCFO-1233zd to form HFO-1234ze. U.S. Pat. No. 6,124,510 teaches the formation of cis and trans isomers of HFO-1234ze by the dehydrofluorination of HFC-245fa using either a strong base or a chromium-based catalyst in the presence of an oxygen containing gas. U.S. Pat. No. 7,563, 936, which is incorporated herein as a reference, teaches the isomerization of cis-1234ze into trans-1234ze over judiciously selected isomerization catalysts. U.S. Pat. No. 7,485, 760, incorporated herein as a reference, further discloses an integrated process to produce trans-1234ze from 245fa, which comprises: (a) dehydrofluorinating 1,1,1,3,3-pentafluoropropane to thereby produce a result comprising cis-1,3,3,3-tetrafluoropropene, trans-1,3,3,3-tetrafluoropropene and hydrogen fluoride; (b) optionally recovering hydrogen fluoride from the result of step (a); (c) isomerizing at least a portion of the cis-1,3,3,3-tetrafluoropropene into trans-1,3,3, 3-tetrafluoropropene; and (d) recovering trans-1,3,3,3-tetrafluoropropene. In one preferred embodiment of that disclosure, 245fa dehydrofluorination and cis-1234ze isomerization are combined in one reactor vessel and after HF is recovered trans-1234ze is isolated as purified product from the overhead of a distillation column and the mixture of unconverted 245fa and cis-1234ze collected as heavies in the reboiler is recycled back to the reactor.

SUMMARY OF THE INVENTION

Applicants have discovered that small amounts of 1,1,3,3-tetrafluoropropene (1234zc) are also generated during 245fa dehydrofluorination and remained in the heavies. When 1234zc is accumulated to certain amounts it becomes difficult to remove by traditional distillation methods. Due to its unknown toxicity and accumulation in the heavies without an outlet, 1234zc has to be removed from the reaction system. Applicants have come to appreciate the need for means by which 1234zc can be removed with minimum loss of product yield and have developed processes for converting 1234zc into useful products (e.g., 1234ze and 245fa) via isomerization and/or fluorination in efficient and cost effective manners. The present invention advantageously manages 1234zc generated as by-product in the trans-1234ze manufacturing process by converting the 1234zc into at least one of 1234ze and/or 245fa.

Accordingly, one aspect of the present invention provides a method for isomerizing a compound comprising contacting a composition comprising 1,1,3,3-tetrafluoropropene with at least one isomerization catalyst selected from the group consisting of metal halides, halogenated metal oxides, and zero-valent metals or metal alloys, wherein said contacting occurs at a reaction temperature sufficient to isomerize at least a portion of said 1,1,3,3-tetrafluoropropene into 1,3,3,3-tetrafluoropropene.

In another aspect of the invention, provided is a method for producing trans-1,3,3,3-tetrafluoropropene comprising: (a) reacting a hydrofluorocarbon reactant in a first reactor under conditions effective to produce product stream comprising trans-1,3,3,3-tetrafluoropropene, cis-1,3,3,3-tetrafluoropropene, 1,1,3,3-tetrafluoropropene, and hydrogen fluoride, and unconverted hydrofluorocarbon reactant; (b) optionally removing said generated hydrogen fluoride from said product stream; (c) distilling said product stream to produce a purified product stream comprising said trans-1,3,3,3-tetrafluoropropene and a second stream comprising said cis-1,3,3,3-tetrafluoropropene, said 1,1,3,3-tetrafluoropropene, and said unconverted hydrofluorocarbon reactant; (d) contacting said second stream with at least one isomerization catalyst selected from the group consisting of metal halides, halogenated metal oxides, and zero-valent metals or metal alloys, wherein said contacting occurs at a reaction temperature sufficient to isomerize at least a portion of said 1,1,3,3-tetrafluoropropene into isomerized 1,3,3,3-tetrafluoropropene; and optionally (e) recirculating said isomerized 1,3,3,3-tetrafluoropropene to said first reactor.

In another aspect of the invention, provided is a method for producing a fluorinated compound comprising reacting a composition comprising 1,1,3,3-tetrafluoropropene with hydrogen fluoride in the presence of at least one catalyst selected from the group consisting of metal halides and halogenated metal oxides wherein said reacting occurs at a reaction temperature sufficient to convert at least a portion of said 1,1,3,3-tetrafluoropropene into a reaction product comprising at least one of 1,3,3,3-tetrafluoropropene and 1,1,1,3,3-pentafluoropropane.

In yet another aspect of the invention, provided is a method for producing trans-1,3,3,3-tetrafluoropropene comprising: (a) reacting a hydrofluorocarbon reactant in a first reactor under conditions effective to produce product stream comprising trans-1,3,3,3-tetrafluoropropene, cis-1,3,3,3-tetrafluoropropene, 1,1,3,3-tetrafluoropropene and hydrogen fluoride, and unconverted hydrofluorocarbon reactant; (b) optionally removing said generated hydrogen fluoride from said product stream; (c) distilling said product stream to produce a purified product stream comprising said trans-1,3,3,3-tetrafluoropropene and a second stream comprising said cis-1,3,3,3-tetrafluoropropene, said 1,1,3,3-tetrafluoropropene, and said unconverted hydrofluorocarbon reactant; and (d)

contacting said second stream with HF in the presence of at least one catalyst selected from the group consisting of metal halides and halogenated metal oxides, wherein said contacting occurs at a reaction temperature sufficient to convert at least a portion of said 1,1,3,3-tetrafluoropropene into a recycle product comprising at least one of 1,3,3,3-tetrafluoropropene and 1,1,1,3,3-pentafluoropropane.

DETAILED DESCRIPTION OF PREFERRED EMBODIMENTS OF THE INVENTION

The present invention discloses methods for isomerizing 1,1,3,3-tetrafluoropropene and methods for managing 1,1,3,3-tetrafluoropropene in trans-1,3,3,3-tetrafluoropropene manufacturing process. In a preferred embodiment, 1234zc is converted into trans/cis-1234ze with the help of a catalyst in the absence of HF in a separate isomerization reactor. In another preferred embodiment, 1234zc is converted into 1234ze and/or 245fa with the help of a catalyst in the presence of HF in a separate reactor or, more preferably, in the same reactor of 245fa dehydrofluorination.

A. 1234zc Isomerization in the Absence of HF

Figure 1:
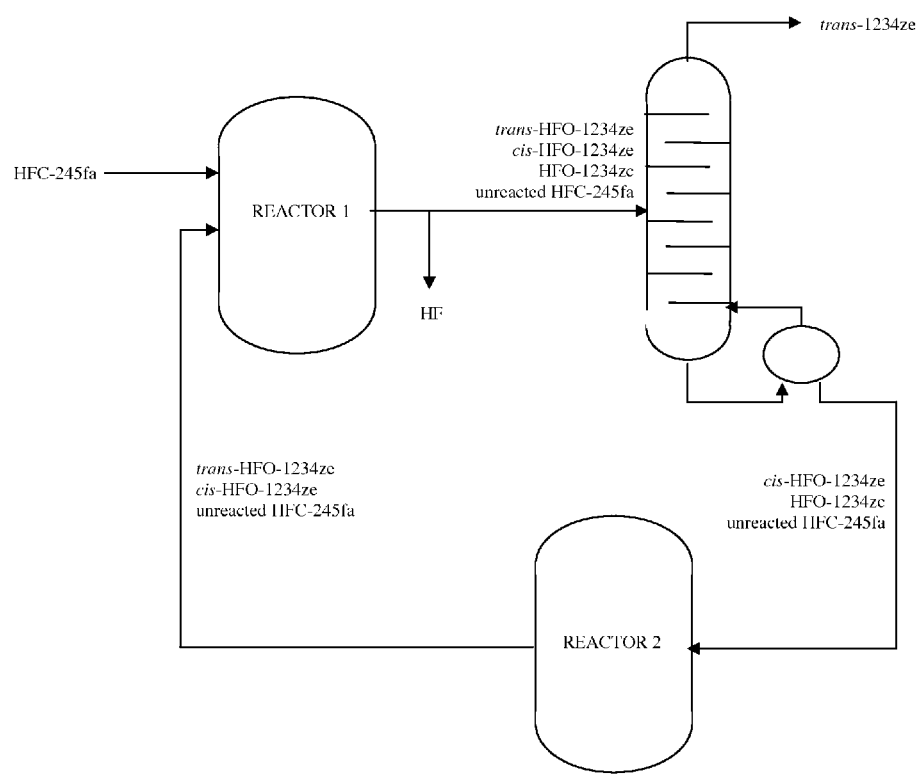
FIG. 1 is a schematic depiction of a process for converting 245fa into 1234ze according to a preferred embodiment of the invention, wherein a 1234zc byproduct is isomerized before being recirculated to a dehydrofluorination reactor.

Referring to FIG. 1, a method of producing trans-1234ze from 245fa according to the present invention is shown. Here, the method involves a recycle loop wherein 1234zc byproduct, along with unreacted 245fa, cis-1234ze are collected as heavies in a reboiler of a distillation column and then fed into an isomerization reactor (Reactor 2) where the 1234zc is converted into trans/cis-1234ze with the help of an isomerization catalyst and in the absence of HF before being recycled back to the reactor of 245fa dehydrofluorination (Reactor 1), preferably a vapor-phase reactor. Three classes of catalysts for this 1234zc isomerization reaction are described as follows:

The first class of isomerization catalysts is metal halides, preferably mono-, bi-, tri-, and tetra-valent metal halides and their mixtures/combinations, more preferably bi-, tri-, and tetra-valent metal halides and their mixtures/combinations, and most preferably tri- and tetra-valent metal halides and their mixtures/combinations. Component metals include, but are not limited to, $Ti^{4+}$, $Zr^{4+}$, $Ce^{4+}$, $Cr^{3+}$, $Al^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. The catalyst may be supported or unsupported.

The second class of catalysts is halogenated metal oxides, preferably halogenated mono-, bi-, tri-, and tetra-valent metal oxides and their mixtures/combinations, more preferably halogenated bi-, tri-, and tetra-valent metal oxides and their mixtures/combinations, and most preferably halogenated tri- and tetra-valent metal oxides and their mixtures/combinations. Component metals include, but are not limited to, $Ti^{4+}$, $Zr^{4+}$, $Ce^{4+}$, $Cr^{3+}$, $Al^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Halogenation treatments can include any of those known in the prior art, particularly those that employ HF, $F_2$, HCl, $Cl_2$, HBr, $Br_2$, HI, and $I_2$ as the halogenation source. The catalyst may be supported or unsupported.

The third class of catalysts is neutral, i.e., zero valent, metals, metal alloys and their mixtures. Useful metals include, but are not limited to, Pd, Pt, Rh, Fe, Co, Ni, Cu, Mo, Cr, Mn, and combinations of the foregoing as alloys or mixtures. The catalyst may be supported or unsupported.

The isomerization reaction is preferably carried out in a gas phase. In less preferred embodiments, it is possible to carry out such reaction in a liquid phase.

Desirable levels of 1234zc conversion and 1234ze selectivity can be impacted by operating parameters, including conditions such as reaction temperature, pressure, and residence time. The reaction will be carried out at conditions sufficient to effect 1234zc isomerization. Selectivity for the isomerization reaction to 1234ze with the preferred catalysts is about 50% or more, more preferably about 70% or more, and most preferably about 95% or more. Conversion of 1234zc is preferably about 10% or more, more preferably about 50% or more, and most preferably about 95% or more.

Isomerization can be carried out at a temperature sufficient to achieve desired conversion level. Reaction temperature refers to the average temperature in the catalyst bed. The reaction temperature preferably ranges from about 50° C. to about 400° C., more preferably from about 100° C. to about 350° C., and most preferably from about 120° C. to about 300° C.

Isomerization can be carried out over a wide range of pressures, as pressure is not a particularly critical reaction condition. Reactor pressure can be superatmospheric, atmospheric, or under vacuum. In preferred embodiments however, the reaction is carried out under pressure conditions ranging from about 1 to about 20 atm and more preferably from about 2 to about 6 atm.

Isomerization can be carried out over a wide range of residence times, as residence time is not a particularly critical reaction condition. In preferred embodiments however, residence time may range from about 0.5 second to about 600 seconds and more preferably from about 10 to about 60 seconds.

B. 1234zc Isomerization and/or Fluorination in the Presence of HF

Figure 2:
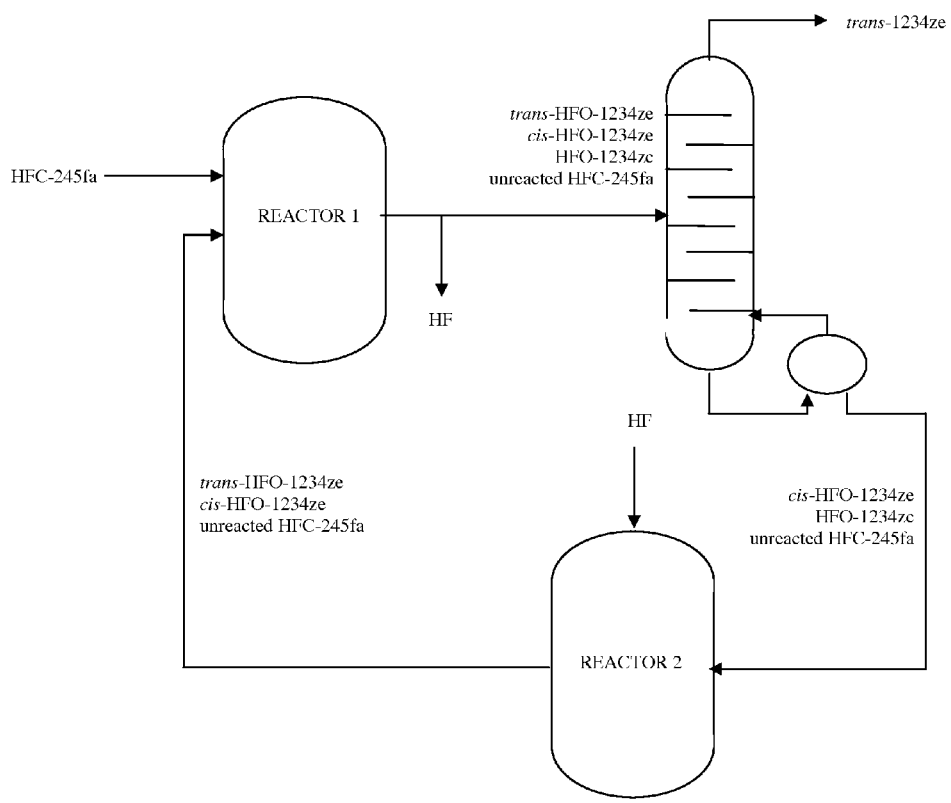
FIG. 2 is a schematic depiction of a process for converting 245fa into 1234ze according to a preferred embodiment of the invention, wherein a 1234zc byproduct is isomerized and/or fluorinated in the presence of HF before being recirculated to a dehydrofluorination reactor.
Figure 3:
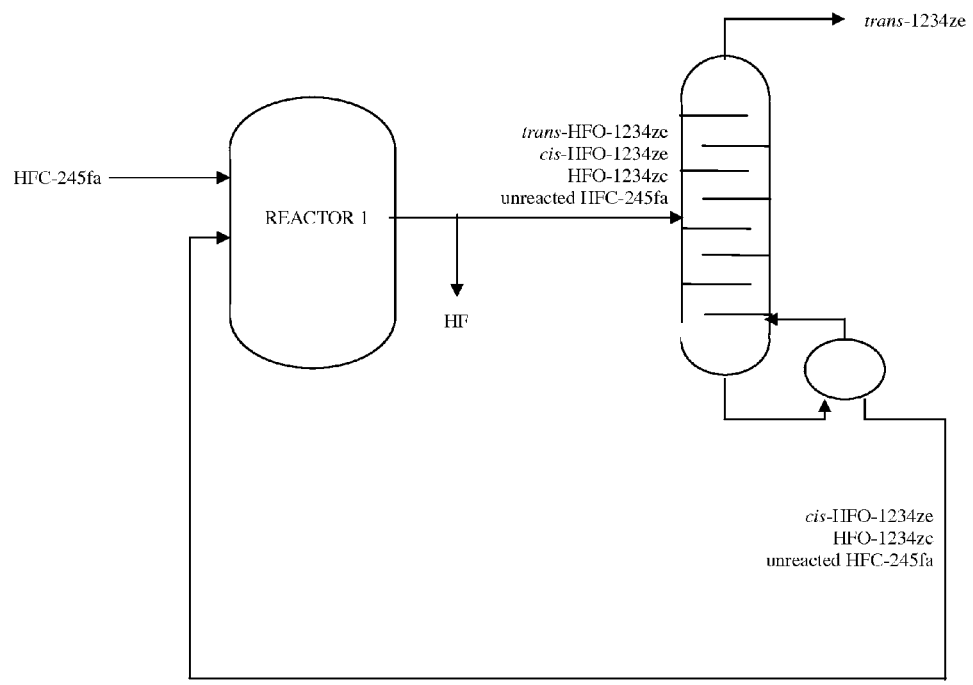
FIG. 3 is a schematic depiction of a process for converting 245fa into 1234ze according to a preferred embodiment of the invention, wherein a 1234zc byproduct is isomerized and/or fluorinated after being recirculated to a dehydrofluorination reactor.

Referring to FIG. 2, the mixture of 245fa, cis-1234ze, and 1234zc are collected as heavies in a reboiler of distillation column and are co-fed together with HF into a separate reactor (Reactor 2) to convert 1234zc into 1234ze and/or 245fa with the help of a catalyst before being recycled back to the reactor of 245fa dehydrofluorination (Reactor 1). Here, a derivate of said bottoms stream is recycled to Reactor 1. FIG. 3 shows another embodiment, which is more preferred, wherein the mixture of 245fa, cis-1234ze, and 1234zc is directly recycled back to the reactor of 245fa dehydrofluorination, in which 1234zc is converted into 1234ze and/or 245fa by reacting with HF (which is generated from 245fa dehydrofluorination in this case) with the help of a catalyst. In this case, the conversion of 1234zc to either 245fa or 1234ze is conducted under the same or similar conditions (catalyst, temperature, pressure, and residence time) as those used in the 245fa to 1234ze conversion. Generally, these reaction parameters are within the ranges cited for the embodiments using FIG. 1 or FIG. 2.

Two classes of catalysts for this 1234zc isomerization reaction are described as follows:

The first class of catalysts is metal halides, preferably mono-, bi-, tri-, and tetra-valent metal halides and their mixtures/combinations, more preferably bi-, tri-, and tetra-valent metal halides and their mixtures/combinations, and most preferably tri- and tetra-valent metal halides and their mixtures/combinations. Component metals include, but are not limited to, $Ti^{4+}$, $Zr^{4+}$, $Ce^{4+}$, $Cr^{3+}$, $Al^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. The catalyst may be supported or unsupported.

The second class of catalysts is halogenated metal oxides, preferably halogenated mono-, bi-, tri-, and tetra-valent metal oxides and their mixtures/combinations, more preferably halogenated bi-, tri-, and tetra-valent metal oxides and their mixtures/combinations, and most preferably halogenated tri- and tetra-valent metal oxides and their mixtures/combinations. Component metals include, but are not limited to, $Ti^{4+}$, $Zr^{4+}$, $Ce^{4+}$, $Cr^{3+}$, $Al^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Halogenation treatments can include any of those known in the prior art, particularly those that employ HF, $F_2$, HCl, $Cl_2$, HBr, $Br_2$, HI, and $I_2$ as the halogenation source. The catalyst may be supported or unsupported.

The isomerization and/or fluorination reaction is preferably carried out in a gas phase. In less preferred embodiments, it is possible to carry out such reaction in a liquid phase.

Desirable levels of 1234zc conversion and 1234ze and/or 245fa selectivity can be impacted by operating parameters, including conditions such as reaction temperature, feed composition, pressure, and residence time. The reaction will be carried out at conditions sufficient to effect 1234zc isomerization and/or fluorination. Selectivity for the isomerization and/or fluorination reaction to 1234ze and/or 245fa with the preferred catalysts is about 50% or more, more preferably about 70% or more, and most preferably about 95% or more. Conversion of 1234zc is preferably about 10% or more, more preferably about 50% or more, and most preferably about 95% or more.

Isomerization and/or fluorination can be carried out at a temperature sufficient to achieve desired conversion level. Reaction temperature refers to the average temperature in the catalyst bed. The reaction temperature preferably ranges from about 100° C. to about 500° C., more preferably from about 200° C. to about 400° C., and most preferably from about 250° C. to about 300° C. The ratio of 1234zc to HF in the feed preferably ranges from 1:0.1 to 1:10000, more preferably from 1:1 to 1:2000, and most preferably from 1:10 to 1:1500.

Isomerization and/or fluorination can be carried out over a wide range of pressures, as pressure is not a particularly critical reaction condition. Reactor pressure can be superatmospheric, atmospheric, or under vacuum. In preferred embodiments however, the reaction is carried out under pressure conditions ranging from about 1 to about 20 atm and more preferably from about 2 to about 6 atm.

Isomerization and/or fluorination can be carried out over a wide range of residence times, as residence time is not a particularly critical reaction condition. In preferred embodiments however, residence time may range from about 0.5 second to about 600 seconds and more preferably from about 10 to about 60 seconds.

EXAMPLES

The following examples are served to demonstrate that 1234zc can be converted into 1234ze and/or 245fa through the process disclosed in the present invention.

Example 1

1234zc Isomerization in the Absence of HF over Fluorinated $Cr_2O_3$ Catalyst

A Monel tube reactor (0.75"OD×0.625"ID×23.0"L) was charged with 20 ml of catalyst pellets. The reactor was heated by a 12" split tube furnace. A multi-point thermocouple, inserted through catalyst bed, was used to measure the temperature of catalyst bed. A mixture of trans-1234ze, 1234zc, cis-1234ze, and 245fa was passed over this catalyst at a rate of 12 g/h. The reaction was conducted under 0.0 psig and at a temperature that was low enough to make certain that no reaction would occur to 245fa included in the feed. The effluent was analyzed by an on-line GC to determine 1234zc conversion and 1234ze selectivity.

The catalyst used in Example 1 was fluorinated $Cr_2O_3$ catalyst. As shown in Table 1, at both 100° C. and 150° C., compared to feed compositions, the concentrations of both trans-1234ze and cis-1234ze in product stream were increased while the concentration of 1234zc was decreased accordingly and the concentration of 245fa remained almost unchanged, indicating the occurrence of 1234zc isomerization into 1234ze. The conversion of 1234zc at 100 and 150° C. was 58.39 and 100.00%, respectively, and the selectivity to 1234ze was 100.00% in both temperatures. These results indicate that the fluorinated chromia catalyst is not only active but also selective for 1234zc isomerization into 1234ze in the absence of HF.

Example 2

1234zc Isomerization/Fluorination in the Presence of HF over Fluorinated $Cr_2O_3$ Catalyst A Monel tube reactor (2"ID×36"L) was charged with 760 ml of catalyst pellets. The reactor was heated by a sand bath furnace. A multi-point thermocouple, inserted through catalyst bed, was used to measure the temperatures of catalyst bed. A mixture of trans-1234ze, 1234zc, cis-1234ze, and 245fa was passed over this catalyst at a rate of 1.8 lb/h. The reaction was conducted under 5.2 psig and at 250-280° C., which was high enough for 245fa dehydrofluorination to produce 1234ze and HF. Both the feed and the effluent were analyzed by GC to determine the concentrations of 1234zc at the inlet and outlet of reactor.

The catalyst used in Example 2 was fluorinated $Cr_2O_3$ catalyst. As shown in Table 2, at 250-280° C., the concentration of 1234zc was, on average, 33% lower at reactor outlet than at reactor inlet, indicating the occurrence of 1234zc isomerization into 1234ze and/or 1234zc fluorination into 245fa by reacting with HF (which is generated from 245fa dehydrofluorination). These results indicate that it is feasible to keep 1234zc within the recycle loop and avoid accumulation of 1234ze in the recycle stream.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

TABLE 1

1234zc isomerization in the absence of HF over fluorinated chromia catalyst

| Feed composition | | | | | Temp. | Product Composition | | | | | 1234zc | 1234ze |
| --- | --- | --- | --- | --- | --- | --- | --- | --- | --- | --- | --- | --- |
| mol, % | | | | | | mol, % | | | | | | |
| t-1234ze | 1234zc | c-1234ze | 245fa | others | (° C.) | t-1234ze | 1234zc | c-1234ze | 245fa | others | conv., % | sel., % |
| 81.22 | 2.02 | 14.00 | 2.68 | 0.06 | 100 | 81.82 | 0.84 | 14.68 | 2.63 | 0.03 | 58.39 | 100.00 |
| 81.22 | 2.02 | 14.00 | 2.68 | 0.06 | 150 | 82.62 | 0.00 | 14.64 | 2.69 | 0.05 | 100.00 | 100.00 |

TABLE 2

1234zc isomerization/fluorination in the presence of HF over fluorinated chromia catalyst

| | Feed composition | | | | | Product Composition | | | | |
| --- | --- | --- | --- | --- | --- | --- | --- | --- | --- | --- |
| Time h | ppm t-1234ze | ppm 1234zc | % c-1234ze | % 245fa | ppm others | % t-1234ze | ppm 1234zc | % c-1234ze | % 245fa | ppm others |
| 0.7 | 972 | 489 | 34.16 | 65.55 | 1383 | 63.86 | 394 | 12.87 | 23.05 | 1342 |
| 2.7 | 893 | 504 | 34.34 | 65.38 | 1419 | 60.53 | 324 | 11.97 | 27.30 | 1311 |
| 4.7 | 479 | 452 | 33.42 | 66.36 | 1316 | 58.72 | 296 | 11.47 | 29.61 | 1412 |
| 6.7 | 686 | 525 | 34.53 | 65.21 | 1439 | 58.34 | 295 | 11.39 | 30.07 | 1376 |
| 8.7 | 432 | 430 | 33.47 | 66.30 | 1461 | 58.04 | 289 | 11.32 | 30.46 | 1363 |
| 10.7 | 382 | 419 | 32.81 | 66.96 | 1508 | 57.84 | 291 | 11.29 | 30.67 | 1453 |
| 12.7 | 741 | 468 | 34.3 | 65.38 | 1951 | 58.12 | 290 | 11.33 | 30.35 | 1504 |
| 14.7 | 500 | 397 | 33.64 | 66.10 | 1635 | 58.49 | 296 | 11.52 | 29.78 | 1623 |
| 16.7 | 440 | 430 | 33.52 | 66.23 | 1648 | 58.24 | 292 | 11.40 | 30.14 | 1668 |
| 18.7 | 691 | 447 | 33.79 | 65.92 | 1770 | 58.23 | 293 | 11.39 | 30.14 | 1706 |
| 20.7 | 971 | 463 | 33.96 | 65.71 | 1878 | 58.10 | 294 | 11.38 | 30.29 | 1741 |

What is claimed is:

1. A method for producing trans-1,3,3,3-tetrafluoropropene comprising:
reacting a hydrofluorocarbon in a first reactor under conditions effective to produce product stream comprising trans-1,3,3,3-tetrafluoropropene, cis-1,3,3,3-tetrafluoropropene, 1,1,3,3-tetrafluoropropene, hydrogen fluoride, and unconverted hydrofluorocarbon reactant;
optionally removing said generated hydrogen fluoride from said product stream;
distilling said product stream to produce a purified product stream comprising said trans-1,3,3,3-tetrafluoropropene and a second stream comprising said cis-1,3,3,3-tetrafluoropropene, said 1,1,3,3-tetrafluoropropene, and said unconverted hydrofluorocarbon reactant;
contacting said second stream with at least one isomerization catalyst selected from the group consisting of metal halides, halogenated metal oxides, and zero-valent metals or metal alloys, wherein said contacting occurs at a reaction temperature from about 50° C. to about 400° C. to isomerize at least a portion of said 1,1,3,3-tetrafluoropropene into isomerized 1,3,3,3-tetrafluoropropene; and
optionally recirculating said isomerized 1,3,3,3-tetrafluoropropene to said first reactor.

2. The method of claim 1 wherein said hydrofluorocarbon comprises 1,1,1,3,3-pentafluoropropane.

3. A method for producing trans-1,3,3,3-tetrafluoropropene comprising:
dehydrofluorinating a hydrofluorocarbon reactant in a first reactor under conditions effective to produce reaction product stream comprising trans-1,3,3,3-tetrafluoropropene, cis-1,3,3,3-tetrafluoropropene, 1,1,3,3-tetrafluoropropene, hydrogen fluoride, and unconverted hydrofluorocarbon reactant;
optionally removing said generated hydrogen fluoride from said product stream;
distilling said reaction product to produce a purified product stream comprising said trans-1,3,3,3-tetrafluoropropene and a second stream comprising said cis-1,3,3,3-tetrafluoropropene, said 1,1,3,3-tetrafluoropropene, and unconverted hydrofluorocarbon reactant;
recirculating said second stream, or derivative thereof, to said first reactor; and
contacting said second stream with at least one catalyst selected from the group consisting of metal halides and halogenated metal oxides, wherein said contacting occurs in the presence of hydrogen fluoride and at a reaction temperature from about 100° C. to about 500° C. to convert at least a portion of said 1,1,3,3-tetrafluoropropene into at least one of 1,3,3,3-tetrafluoropropene and 1,1,1,3,3-pentafluoropropane.

4. The method of claim 3 wherein said contacting occurs in a second reactor.

5. The method of claim 3 wherein contacting occurs in said first reactor.

6. The method of claim 1 wherein the contacting step occurs at a pressure of about 1 to about 20 atm.

7. The method of claim 1 wherein the contacting step occurs at a pressure of about 2 to about 6 atm.

8. The method of claim 1 wherein the contacting step occurs with a residence time of about 0.5 to about 600 seconds.

9. The method of claim 1 wherein the contacting step occurs with a residence time of about 10 to about 60 seconds.

10. The method of claim 3 wherein 1,1,3,3-tetrafluoropropene is converted into 1,3,3,3-tetrafluoropropene.

11. The method of claim 3 wherein 1,1,3,3-tetrafluoropropene is converted into and 1,1,1,3,3-pentafluoropropane.

12. The method of claim 3 wherein said contacting comprises forming a reaction mixture comprising 1,1,3,3-tetrafluoropropene and hydrogen fluoride in a 1,1,3,3-tetrafluoropropene:hydrogen fluoride ratio of about 1:0.1 to about 1:10000.

13. The method of claim 3 wherein said contacting comprises forming a reaction mixture comprising 1,1,3,3-tetrafluoropropene and hydrogen fluoride in a 1,1,3,3-tetrafluoropropene: hydrogen fluoride ratio of about 1:1 to about 1:2000.

14. The method of claim 3 wherein said contacting comprises forming a reaction mixture comprising 1,1,3,3-tetrafluoropropene and hydrogen fluoride in a 1,1,3,3-tetrafluoropropene:hydrogen fluoride ratio of about 1:10 to about 1:1500.

15. The method of claim 3 wherein at least said contacting step occurs in a vapor phase.

16. The method of claim 3 wherein said contacting step occurs at a pressure of about 1 to about 20 atm.

17. The method of claim 3 wherein said contacting step occurs with a residence time of about 0.5 to about 600 seconds.

\* \* \* \* \*